(12) United States Patent
Izevbigie

(10) Patent No.: US 6,541,196 B2
(45) Date of Patent: Apr. 1, 2003

(54) METHOD FOR CAMP PRODUCTION

(75) Inventor: Ernest B. Izevbigie, Flowood, MS (US)

(73) Assignee: Jackson State University, Jackson, MS (US)

( * ) Notice: Subject to any disclaimer, the term of this patent is extended or adjusted under 35 U.S.C. 154(b) by 0 days.

(21) Appl. No.: 09/911,283

(22) Filed: Jul. 23, 2001

(65) Prior Publication Data

US 2002/0022220 A1 Feb. 21, 2002

Related U.S. Application Data
(60) Provisional application No. 60/221,343, filed on Jul. 26, 2000.

(51) Int. Cl.[7] ................................................. C12Q 1/00
(52) U.S. Cl. .............................. 435/4; 435/29; 435/69.2
(58) Field of Search .............................. 435/4, 29, 69.2

(56) References Cited

PUBLICATIONS

Kercsmar C. Adenosine 3:5' Cyclic Monophosphate Synthesis by Human Tracheal Epithelial Cells. American J of Respiratory Cell and Molecular Bio 2(1)33–39, 1990.*

Sigiyama A. An Enzymatic Fluorometric Assay for Adenosine 3':5'–Monophosphate. Analytical Biochem 218 20–25, 1994.*

Suidan H. Simultaneous Analysis of Adenosine 3',5'–cyclic Monophosphate . . . Anal Biochem 205(1)159–165, 1992.*

Ethier M. Mechanism of Enhanced cAMP Stimulation by Isoproterenol in Aged Human Fibroblasts. Exp Gerontology 27(3)287–300, 1992.*

Izevbigie, E.B. and Bergen, W.G. (2000) *Beta–adrenergic agonist hyperplastic effect is associated with increased fibronectin gene expression and not mitogen–activated protein kinase modulation in C2C12 cells, Proc. Soc. Exp. Biol. Med.* 223:302–309.

Izevbigie, E.B., Gutkind, J.S., and Ray, P.E. (2000) Angiotensin II and basic fibroblast growth factor mitogenic pathways in human fetal mesangial cells, *Pediatr. Res.* 47:614–621.

Izevbigie, E.B., Gutkind, J.S., and Ray, P.E. (2000) Isoproterenol inhibits fibroblast growth factor–2 growth of renal epithelial cells, *Pediatr. Nephrol.* 14:726–734.

Tovey, K.C., Oldham, K.G., Whelan, J.A., (1974) A simple direct assay for cyclic AMP in plasma and other biological samples using an improved competitive binding technique. *Clin. Chim. Acta* 56:221–234.

* cited by examiner

*Primary Examiner*—Ralph Gitomer
(74) *Attorney, Agent, or Firm*—Howrey Simon Arnold & White, LLP

(57) ABSTRACT

The present invention provides for novel methods for measuring the levels of cyclic adenosine monophosphate (cAMP) produced by cells. Notably, the methods provided do not require that the cell membranes be disrupted. Specifically, the present invention provides for a methods of detecting and quantifying cAMP extracellularly and for kits useful in employing these methods. Furthermore the present invention also provides for a method of isolating cAMP produced by cell culture.

5 Claims, 4 Drawing Sheets

METHOD FOR CAMP PRODUCTION

This application claims priority to Provisional Application Ser. No. 60/221,343 filed Jul. 26, 2000.

BACKGROUND OF THE INVENTION

1. Field of the Invention

The present invention relates generally to the fields of detecting, quantifying and purifying chemicals responsible for cellular signaling. The instant invention concerns a novel method for measuring the levels of cyclic adenosine monophosphate (cAMP) produced by cells which does not require that the cells be lysed. Specifically, the present invention provides for a method of detecting and quantifying cAMP extracellularly and for kits useful in employing these methods. Additionally, the instant invention provides for a method of isolating cAMP produced by cell culture.

2. Technical Problem Addressed by the Invention

A. Measurement for cAMP for Intact Cells

Heretofore in the field of cell signaling, in order to measure the level of cAMP produced by a cell during a cell-signaling event, it has been necessary to break open (or lyse) the cells. The instant invention provides for a method of measuring cellular cAMP levels without lysing the cells. This is advantageous because it allows for the continued growth and monitoring of the cells whose cAMP levels are being monitored.

A related problem has been the high cost of producing cAMP for experimental and other uses. cAMP is typically produced today by expensive synthetic chemical means. The instant invention also provides for a more cost-effective method of producing cAMP by doing so in a tissue culture or bio-reactor system.

SUMMARY OF THE INVENTION

The present invention provides for a method of measuring and producing cAMP in a cell culture or bioreactor system. The instant invention also provides for kits useful for measuring cAMP in these types of systems.

One embodiment of the instant invention provides for a method of measuring the cAMP concentrations produced by cells without disrupting the cell's membranes. This method comprises the following steps:
 a) Providing cells growing in culture.
 b) Removing the growth media from the cells.
 c) Adding cAMP collection medium to the cells.
 d) Incubating said cells with said collection medium.
 e) Removing the collection medium and determining the cAMP concentration in the collection medium.

Another aspect of this embodiment of the invention provides for a kit for use to determine the amounts of cAMP produced by cells.

Another embodiment of the instant invention provides for a method of producing cAMP from tissue culture or a bioreactor. One aspect of this embodiment of the invention comprises the steps of:
 a) Providing a culture of cells.
 b) Removing the growth media from the cells.
 c) Adding a cAMP collection medium.
 d) Incubating said cells with said collection medium.
 e) Removing the collection medium, and purifying the cAMP from the collection medium.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
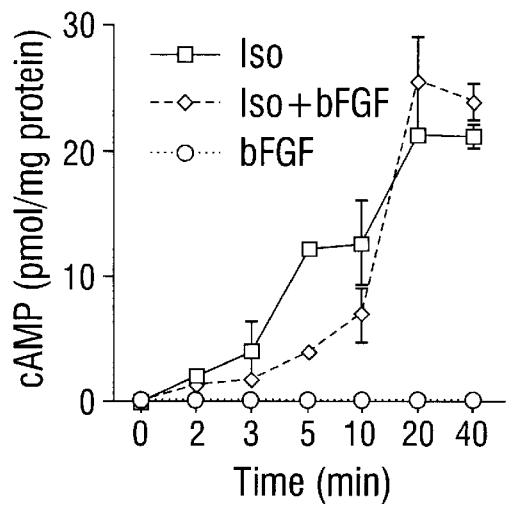
FIG. 1a. shows the effect of bFGF on isoproterenol stimulated cAMP accumulation in $MDCK_{E11}$ cells. 1b. Shows isoproterenol induction of cAMP production in $MDCK_{E11}$ cells: $P<0.001$ when compared to all other groups. 1c. Shows the effect of bFGF on isoproterenol-stimulated cAMP accumulation in human RPTEc; $P<0.001$ when compared to all other groups. 1d. Shows the effect of bFGF and isoproterenol on cAMP accumulation in human RPTEc **$P<0.001$ when compared to all other groups (ISO=isoproterenol; bFGF=basic fibroblast growth factor; RPTEc=renal proximal tubular epithelial cells).
Figure 1C:
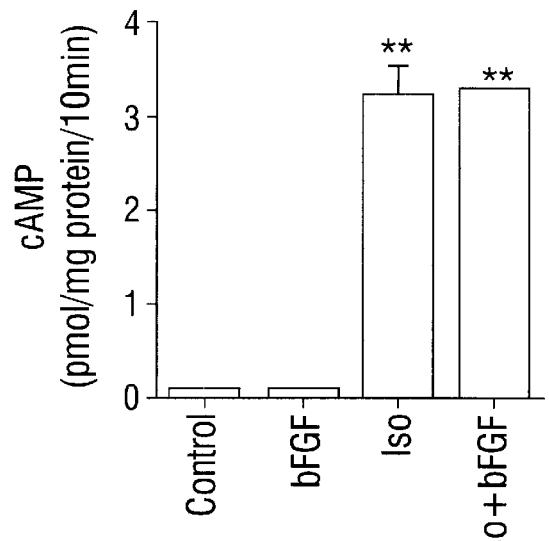
Figure 1B:
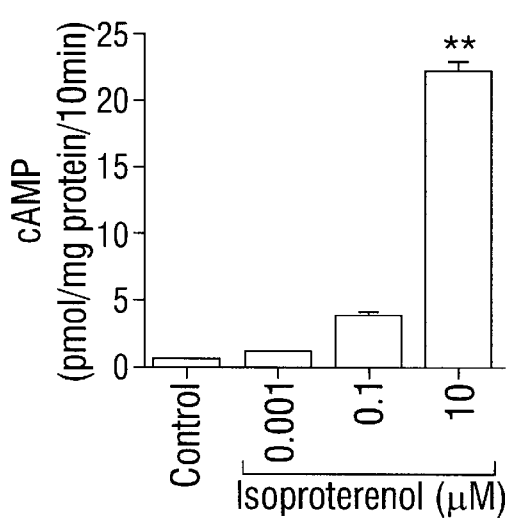
Figure 1D:
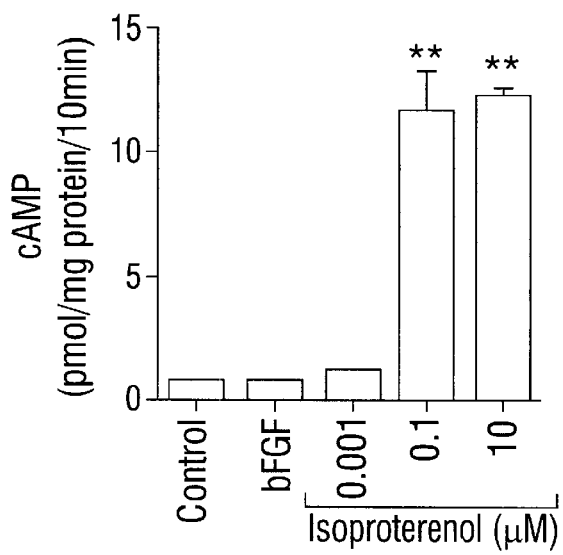

The present invention provides for methods of measuring and producing cAMP in a cell culture or bioreactor system. The instant invention also provides for kits useful for measuring cAMP in these types of systems.

One embodiment of the instant invention provides for a method of measuring the cAMP concentrations produced by cells without disrupting the cell's membranes. This method comprises the following steps:
 a) Providing cells growing in culture.
 b) Removing the growth media from the cells.
 c) Adding cAMP collection medium to the cells.
 d) Incubating said cells with said collection medium.
 e) Removing the collection medium and determining the cAMP concentration in the collection medium.

In this aspect of the instant invention it is contemplated that the cAMP levels may be determined in any suitable cell type. Preferably, cAMP levels may be determined in any cell type selected from the group consisting of mammalian, avian, and insect cells. More preferably the cells are mammalian or avian cells. Even more preferably the cells are myoblasts, mesangial cells, or renal epithelial cells.

The cells may be grown in any suitable medium as understood by one of ordinary skill in the art as being appropriate for the cell type. The growth medium may be removed by any method compatible with the instant invention. Exemplary methods include aspiration and centrifugation followed by aspiration depending on whether the cultured cells are anchored or suspended.

Prior to adding the cAMP collection medium it is preferable to wash the cells at least once to remove any residual growth medium which may interfere with subsequent cAMP analysis. Solutions suitable for use as wash solutions are well known in the art and include, but are not limited to, phosphate and TRIS (trishydroxyaminomethane) buffered saline solutions such as PBS and STE. An exemplary wash solution is phosphate buffered saline (PBS) at a pH of 7.5 which has been warmed to the normal incubation temperature of the cells which are to be washed (e.g. 37° C. for human cells). In order to prevent enzymatic degradation of the cAMP the collection medium typically comprises a cAMP phosphodiesterase inhibitor. Such inhibitors are known in the art. Any inhibitor compatible with the instant invention is contemplated for use in this embodiment of the invention. A preferred cAMP phosphodiesterase inhibitor is imidazolidin [4-(3-butoxy-4-methodxy-benzyl) imidazolidin-2-one] (Sigma cat. no. B 8279). Such substances are to be used at the concentration typically used by those skilled in the art. For example imidazolidin is used at a final concentration of 10 $\mu$M.

In another aspect of this embodiment it is envisioned that the cells may be treated with a compound which stimulates cAMP production. This treatment may be either prior to, during, or both prior to and during the incubation with the cAMP collection medium. Any substance which initiates a signal transduction cascade resulting in the production of cAMP which is compatible with the instant invention is contemplated as useful for this aspect of the invention. Exemplary substances include, but are not limited to forskolin and isoproterenol.

Following the collection of the cAMP collection medium, the medium is preferably concentrated prior to analyzing the cAMP content of the medium. One method of concentrating the collection medium which is preferably considered for this aspect of the instant invention is concentration by lyophilization. Following concentration, the cAMP sample may be diluted, as necessary, in an appropriate diluent. One exemplary diluent contemplated for use in this aspect of the instant invention is a Tris-EDTA solution at pH 7.5.

Another aspect of this embodiment of the invention provides for a diagnostic kit useful for determining the amounts of cAMP produced by cells. Kits according to this embodiment of the invention may comprise packages, each containing one or more of the various reagents (typically in concentrated form) which are required to perform the diagnostic tests.

Another embodiment of the instant invention provides for a method of producing cAMP from tissue culture or a bioreactor. One aspect of this embodiment of the invention comprises the steps of:

a) Providing a culture of cells.
b) Removing the growth media from the cells.
c) Adding a cAMP collection medium.
d) Incubating said cells with said collection medium.
e) Removing the collection medium, and purifying the cAMP from the collection medium.

For the production of cAMP, the cells may be grown in any medium understood by one of ordinary skill in the art to be appropriate for the particular cell type. The growth medium may be removed by an method compatible with the instant invention. Exemplary methods include aspiration and centrifugation followed by aspiration depending on whether the cultured cells are anchored or suspended.

Prior to adding the cAMP collection medium it is preferable to wash the cells at least once to remove any residual growth medium which may interfere with subsequent cAMP analysis. Solutions suitable for use as wash solutions are well known in the art and include, but are not limited to, phosphate and TRIS (trishydroxyaminomethane) buffered saline solutions such as PBS and STE. An exemplary wash solution is phosphate buffered saline (PBS) at a pH of 7.5 which has been warmed to the normal incubation temperature of the cells which are to be washed (e.g. 37° C. for human cells). In order to prevent enzymatic degradation of the cAMP the collection medium typically comprises a cAMP phosphodiesterase inhibitor. Such inhibitors are known in the art. Any inhibitor compatible with the instant invention is contemplated for use in this embodiment of the invention. A preferred cAMP phosphodiesterase inhibitor is imidazolidin [4-(3-butoxy-4-methodxy-benzyl) imidazolidin-2-one] (Sigma cat. no. B 8279). Such substances are to be used at the concentration typically used by those skilled in the art. For example, imidazolidin is used at a final concentration of 10 $\mu$M.

In another aspect of this embodiment, it is envisioned that the cells may be treated with a compound which stimulates cAMP production. This treatment may be either prior to, during, or both prior to and during the incubation with the cAMP collection medium. Any substance which initiates a signal transduction cascade resulting in the production of cAMP which is compatible with the instant invention is contemplated as useful for this aspect of the invention. Exemplary substances include, but are not limited to, forskolin and isoproterenol.

Following the collection of the cAMP collection medium, the medium is preferably concentrated prior to analyzing the cAMP content of the medium. One method of concentrating the collection medium which is preferably considered for this aspect of the instant invention is concentration by lyophilization. Following concentration, the cAMP sample may be diluted, as necessary, in an appropriate diluent. One exemplary diluent contemplated for use in this aspect of the instant invention is a Tris-EDTA solution at pH 7.5.

In order to provide sufficient amounts of cAMP to be commercially useful, it is contemplated that the cells of this aspect of the instant invention may be grown in large quantities, in a commercial bioreactor, for example.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Quantitation of cAMP in Renal Tubular Epithelial Cells (RTEc)

The culture medium was aspirated from RTEc monolayers, and the cells were washed three times with PBS. Madin-Darby canine kidney cell (MDCKc) monolayers were then overlaid with 5 mls PBS at room temperature on 100 mm culture dishes. cAMP phosphodiesterase inhibitor was added at a final concentration of 10 $\mu$M to all incubations to prevent the enzymatic degradation of cellular cAMP. Isoproterenol (ISO) at $10^{-5}$M, bFGF (basic fibroblast growth factor) (20 ng/ml), or both were added to the treatment groups. Cells were incubated under an atmosphere of 95% air and 5% $CO_2$ at 37° C. for 1, 3, 5, 10, 20, and 40 minute periods. Following the incubation period, 1.0 ml/plate aliquot samples were transferred to 12×75 mm polypropylene tubes, and immediately placed in a 0° C. ice bath. The cell monolayers and 1.0 ml aliquots were stored at −20° C. for protein determination and cAMP analysis respectively. Total cellular protein was determined using the BCA (bicinchoninic acid) protein assay (Pierce, Rockford, Ill.) according to the manufacturers specification. The cAMP assays were done as prescribed by the manufacturer of the cAMP quantitation kit (Diagnostic Products Corporation, Los Angeles, Calif.); this procedure is patterned after a procedure described by Tovey et al. The procedure entails a competition of $^3$H cAMP for cAMP binding protein, separation of free (unbound) cAMP by adsorption onto dextran-coated charcoal, followed by counting of bound $^3$H by liquid scintillation (Izevbigie, *Pediatr. Nephrol.*, 2000). See FIG. 1 for results.

Example 2

Quantitation of cAMP in Mouse $C_2C_{12}$ Myoblasts

Figure 2:
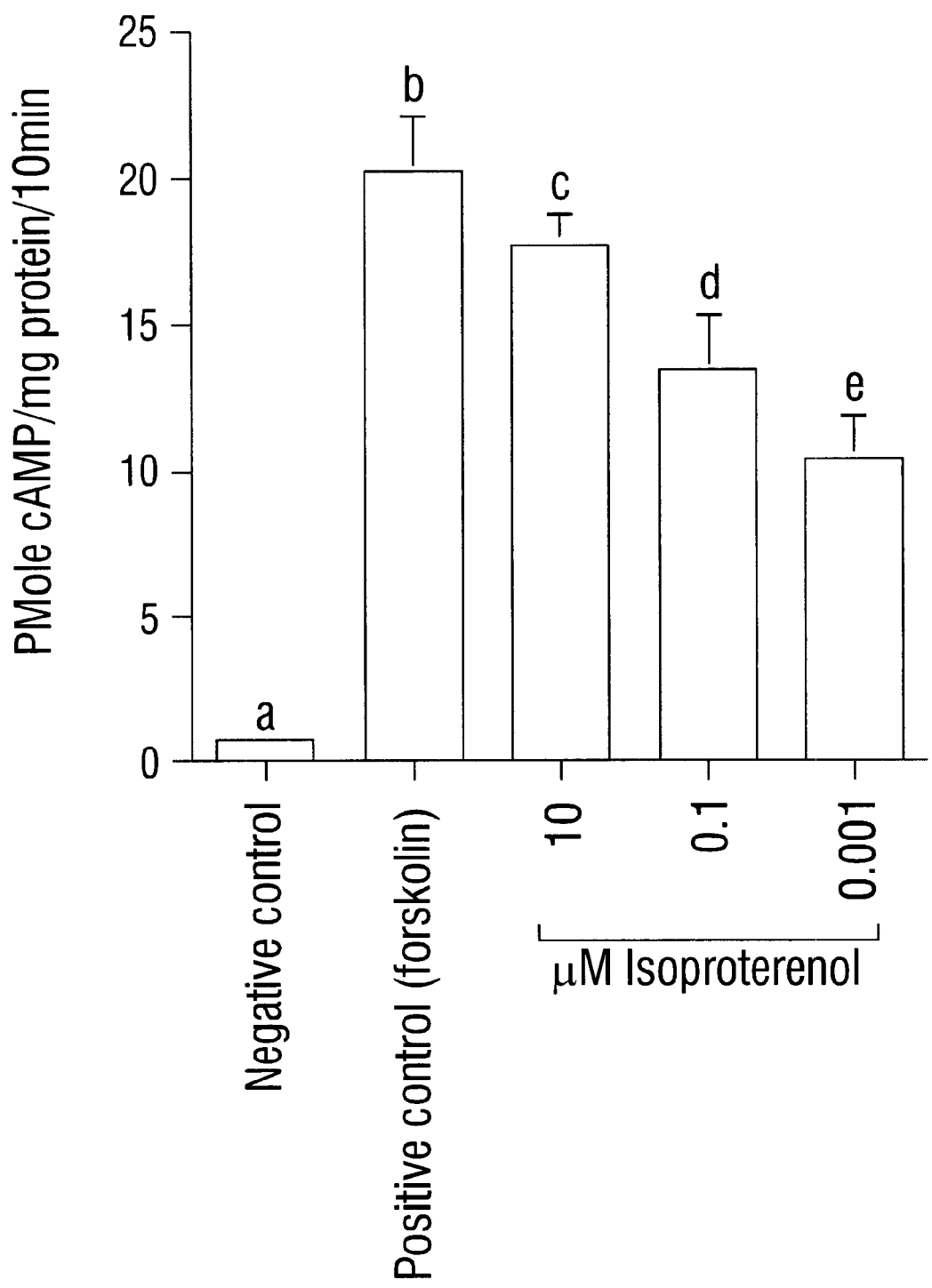
FIG. 2 Shows Isoproterenol dose-dependent cAMP production in differentiated $C_2C_{12}$ cells. $C_2C_{12}$ cells were propagated and differentiated. Cells were treated with either forskolin (50 $\mu$M) or isoproterenol (10, 0.1, or 0.001 $\mu$M) final concentrations. Monolayers were then incubated at 37° C. for 10 min. and cAMP was quantified. Each data point represents mean±SD for three independent experiments. Means (positive control, ISO at 0.001, 0.1, 10 $\mu$M) not sharing common letter were different $P<0.05$.

Medium was aspirated from differentiated $C_2C_{12}$ cells, and monolayers were washed with PBS. Monolayers were then overlaid with PBS at 37° C. containing the following treatments: isoproterenol (ISO) at $10^{-5}$, $10^{-7}$, and $10^{-9}$ M forskolin (positive control) at $5 \times 10^{-5}$ M, and negative control (no treatments). A cAMP phosphodiesterase inhibitor, imidazolidin, ($10^{-6}$ M) was added to all incubations to prevent enzymatic degradation of cAMP. Culture dishes were placed in a humidified incubator under an atmosphere of 95% air and 5% $CO_2$ at 37° C. for 5–10 min. After the incubation, aliquots of incubation medium were quickly removed, chilled, and stored at −20° C. for cAMP determination (within 3 days). Cells were washed and frozen for later protein determination (Bradford, 1976). The cAMP assays were done as prescribed by the manufacturer of the cAMP quantitation kit (Diagnostic Products Corporation, Los Angeles, Calif.); this procedure is patterned after a procedure described by Tovey et al. The procedure entails a competition of $^3$H cAMP for cAMP binding protein, separation of free (unbound) cAMP by adsorption onto dextran-coated charcoal, followed by counting of bound $^3$H by liquid scintillation. Preliminary work showed that stimulation of the $\beta$-AR adenylyl-cyclase system in $C_2C_{12}$ myoblasts in the presence of 4-(3-butoxy-4-methoxy-benzyl) imidazolidin (a phosphodiesterase inhibitor) resulted in cAMP accumulation within the cells coupled with some accumulation in the incubation media (PBS). Thus, cAMP production was determined as the sum of assayable cAMP in the PBS and within the cells. Time course studies showed a linear cAMP production response up to 10 min (see FIG. 2) (Izevbigie and Bergen, 2000).

Example 3

Quantitation of cAMP in Human Fetal Mesangial Cells (HFMc)

Figure 3:
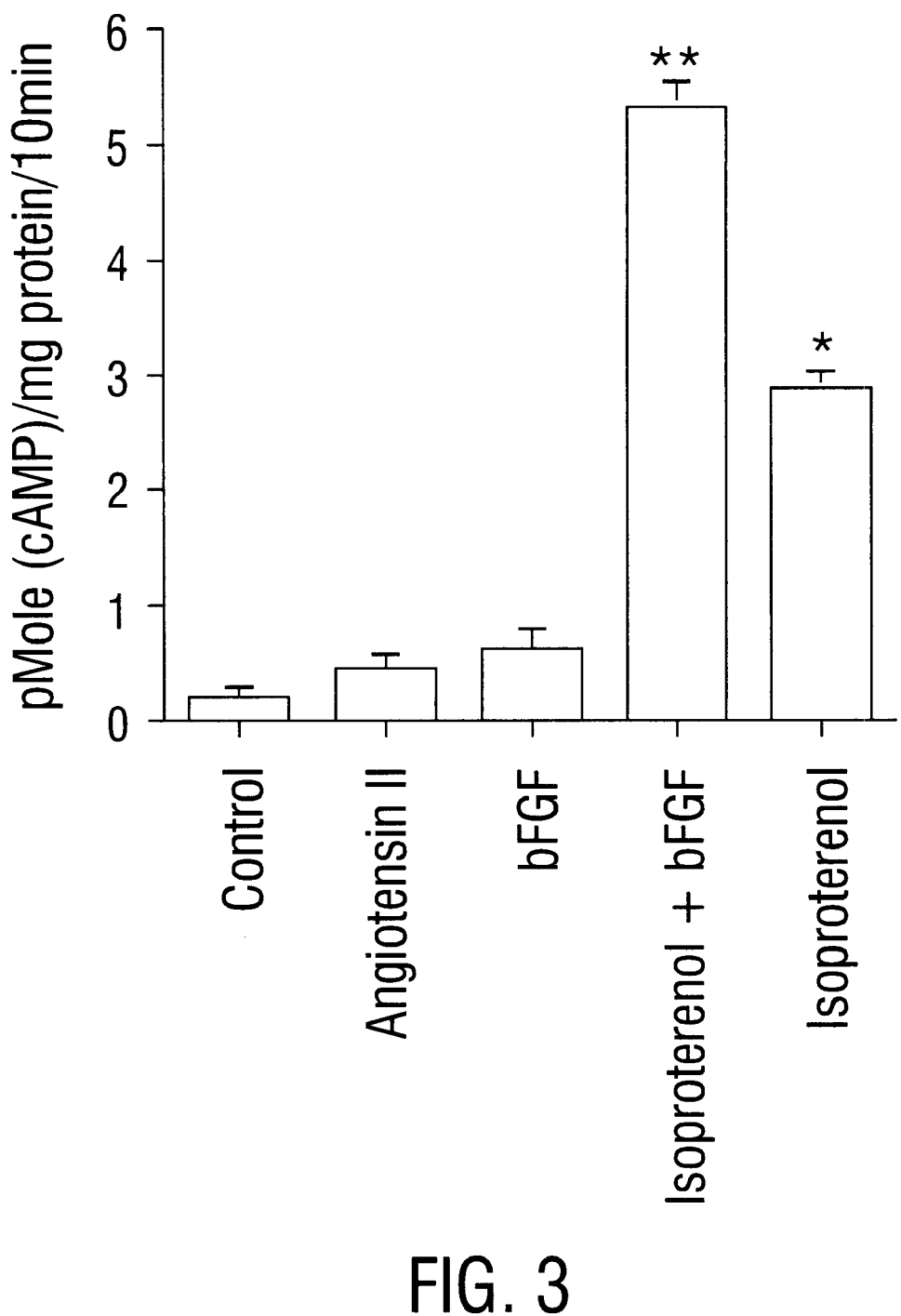
FIG. 3. Shows the effects of Ang II, bFGF, and isoproterenol on cAMP accumulation in HFMc. Confluent HFMc were serum-starved overnight before treatment with PBS (control), Ang II 1 $\mu$M, bFGF 20 ng/ml, and isoproterenol 10 $\mu$M in combination with bFGF or alone for 10 min. cAMP assays were done. The results represent the mean±SD for three independent experiments performed in triplicate each time. Basic FGF but not Ang II induced a modest but significant increase in cAMP accumulation ($p<0.05$) when compared with control cells *$p<0.005$ when compared with control, Ang II, and bFGF groups, **$p<0.05$ when compared with all other groups.
Figure 4:
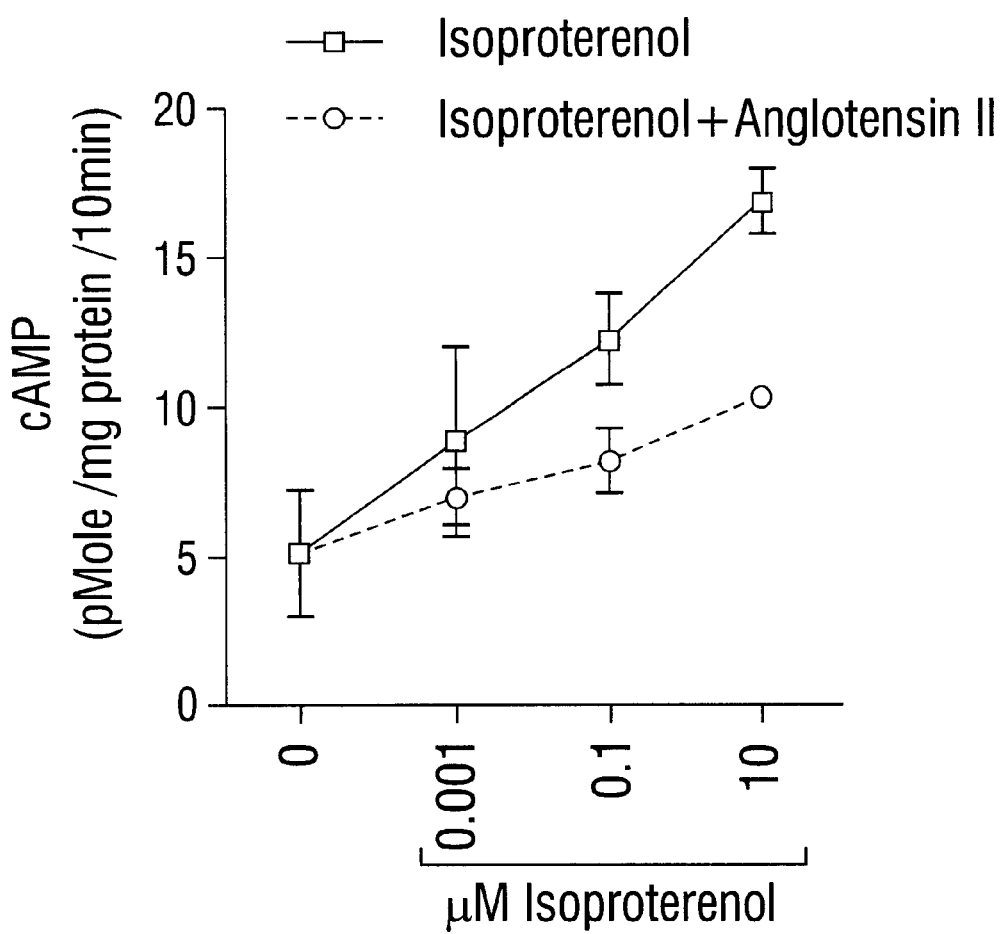
FIG. 4. Shows modulation of isoproterenol-induced cAMP accumulation by Ang II in HFMc. Confluent HFMc were serum-starved overnight before treatment with Ang II (1 M) or different concentrations of isoproterenol for 10 min. Ang II decreased the accumulation of cAMP induced by isoproterenol. Results represent the mean±SD values of three different experiments performed in triplicate each time. Differences between isoproterenol and isoproterenol with Ang II-treated cells at 0.1 and 10 $\mu$M isoproterenol concentrations were significantly different ($p<0.05$).

The culture medium was aspirated from HFMc monolayers, and the cells were washed three times with PBS. Cell monolayers were then overlaid with PBS at room temperature on 100 mm culture dishes. A cAMP phosphodiesterase inhibitor was added to a final concentration of 10 $\mu$M to all incubations to prevent the enzymatic degradation of cellular cAMP. Isoproterenol (ISO) at $10^{-5}$M, with or without bFGF (basic fibroblast growth factor) (20 ng/ml), or three doses of ISO ($10^{-5}$, $10^{-7}$, $10^{-9}$M) with $10^{-6}$M angiotensin II (Ang II) were added to the treatment groups. Cells were incubated under an atmosphere of 95% air and 5% $CO_2$ at 37° C. for 10 minutes. Following the incubation period, 1.0 ml/plate aliquot samples were transferred to 12×75 mm polypropylene tubes, and immediately placed in a 0° C. ice bath. The cell monolayers and 1.0 ml aliquots were stored at −20° C. for protein determination and cAMP analysis respectively. Total cellular protein was determined using the BCA (bicinchoninic acid) protein assay (Pierce, Rockford, Ill.) according to the manufacturers specification. The extracellular cAMP per plate was quantified using Diagnostic Corporation (Los Angeles, Calif.) kits according to the manufacturer's specifications; this procedure is patterned after a procedure described by Tovey et al. The procedure entails a competition of $^3$H cAMP for cAMP binding protein, separation of free (unbound) cAMP by adsorption onto dextrancoated charcoal, followed by counting of bound $^3$H by liquid scintillation (Izevbigie, *Pediatr. Res.*, 2000). See FIGS. 3 and 4 for results.

All of the methods and kits disclosed and claimed herein can be made and executed without undue experimentation in light of the present disclosure. While the compositions and methods of this invention have been described in terms of preferred embodiments, it will be apparent to those of skill in the art that variations may be applied to the methods and kits and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bradford, M. M., (1976) *A rapid sensitive method for the quantification of microgram quantities of protein utilizing the principle of protein dye-binding. Anal. Biochem.* 72:248–254.

Izevbigie, E. B. and Bergen, W. G. (2000) *Beta-adrenergic agonist hyperplastic effect is associated with increased fibronectin gene expression and not mitogen-activated protein kinase modulation in C2C12 cells, Proc. Soc. Exp. Biol. Med.* 223:302–309.

Izevbigie, E. B., Gutkind, J. S., and Ray, P. E. (2000) *Angiotensin II and basic fibroblast growth factor mitogenic pathways in human fetal mesangial cells, Pediatr. Res.* 47:614–621.

Izevbigie, E. B., Gutkind, J. S., and Ray, P. E. (2000) *Isoproterenol inhibits fibroblast growth factor-2 growth of renal epithelial cells, Pediatr. NeDhrol. In press.*

Tovey, K. C., Oldham, K. G., Whelan, J. A., (1974) *A simple direct assay for cyclic AMP in plasma and other biological samples using an improved competitive binding technique. Clin. Chim. Acta* 56:221–234.

What is claimed is:

1. A method of producing cyclic-adenosine monophosphate (cAMP), extracellularly, from cultured cells, said method comprising;
   a) providing a culture of cells in a growth medium,
   b) removing the growth medium from the cells,
   c) adding a cAMP collection medium,
   d) incubating said cells with said collection medium without disrupting the cells' membranes,
   e) removing the collection medium from the cells, and
   f) purifying the cAMP from the collection medium.

2. The method of claim 1 wherein the cells are selected from the group consisting of mammalian, avian and insect cells.

3. The method of claim 1 further comprising concentrating the collection medium prior to purifying the cAMP.

4. The method of claim 1, wherein the cells are mammalian cells; wherein the collection medium comprises a buffered saline solution, isoproterenol and imidazolidin.

5. The method of claim, 4, further comprising determining the cAMP concentration; wherein the cells are selected from the group consisting of Madin-Darby canine kidney cells, mouse $C_2C_{12}$ myoblasts, and human fetal mesangial cells; wherein the collection medium comprises phosphate-buffered saline (pH 7.5); wherein the collection medium is concentrated by lyophilization prior to determining the cAMP concentration, and wherein the cAMP concentration is determined by liquid scintillation.

* * * * *